(12) United States Patent
DiNardo et al.

(10) Patent No.: US 8,802,054 B2
(45) Date of Patent: Aug. 12, 2014

(54) METHOD FOR CHARACTERIZING THE OXIDATIVE STRESS PROTECTIVE CAPACITY OF AN ANTIOXIDATIVE SUBSTANCE

(75) Inventors: Joseph C. DiNardo, Vesuvius, VA (US); Joseph A. Lewis, II, Chesterfield, VA (US)

(73) Assignee: PCR Technology Holdings, LC, Richmond, VA (US)

( * ) Notice: Subject to any disclaimer, the term of this patent is extended or adjusted under 35 U.S.C. 154(b) by 3099 days.

(21) Appl. No.: 11/050,571

(22) Filed: Feb. 3, 2005

(65) Prior Publication Data

US 2006/0171886 A1 Aug. 3, 2006

(51) Int. Cl.
*A61K 49/00* (2006.01)
*A61Q 17/04* (2006.01)
*A61K 8/67* (2006.01)
*A61K 9/00* (2006.01)

(52) U.S. Cl.
CPC .............. *A61Q 17/04* (2013.01); *A61K 8/678* (2013.01); *A61K 9/0014* (2013.01); *A61K 2800/522* (2013.01)
USPC ........................................... 424/9.1; 424/9.2

(58) Field of Classification Search
None
See application file for complete search history.

(56) References Cited

U.S. PATENT DOCUMENTS

| | | | |
|---|---|---|---|
| 5,523,429 A | 6/1996 | Ghyczy | |
| 6,015,548 A | 1/2000 | Siddiqui et al. | |
| 6,433,025 B1 | 8/2002 | Lorenz | |
| 6,569,683 B1* | 5/2003 | Ochi et al. | 436/63 |
| 6,756,045 B1 | 6/2004 | Neudecker et al. | 424/401 |
| 7,132,296 B2 | 11/2006 | Ou et al. | |
| 2005/0025727 A1 | 2/2005 | Lott | |
| 2005/0233471 A1* | 10/2005 | McEwan et al. | 436/173 |
| 2007/0036675 A1 | 2/2007 | Ou et al. | |

OTHER PUBLICATIONS

DiNardo et al. (American Academy of Dermatology 62nd Annual Meeting, Feb. 6-11, 2004; whole abstract).*
Neudecker et al. (American Academy of Dermatology, San Francisco, 61st Annual Meeting, Mar. 21-26, 2003; whole abstract).*
Weber et al. (Free Radical Biology & Medicine 1997, 22, 761-769).*
Mitchell et al. (Arch. Biochem. Biophys. 1998, 360, 142-148).*
Zhai et al. (Skin Research and Technology 2003, 9, 254-256).*
Benzie et al. (Analyt. Biochem. 1996, 239, 70-76).*
Trolox (Wikipedia).*
Pulido et al. (Eur. J. Clin. Nutrition 2003, 57, 1275-1282).*
Trolox (wikipedia) 2010.*
Boxin OU et al. "Development and Validation of an Improved Oxygen Radical Absorbance Capacity Assay Using Flurorescein as the Fluorescent Probe", J. Agric. Food Chem. 2001, 49, pp. 4619-4626.
Dejian Huang et al. "Developement and Validation of Oxygen Radical Absorbance Capacity Assay for Lipophilic Antioxidants Using Randomly Methylated ss—Cyclodextrin as the Solubility Enhacer", J. Agric. Food Chem. 2002, 50, pp. 1815-1821.
Ou, Boxin et al., Prior, Ronald L., Hampsch-Woodill, Maureen, "Development and Validation of an Improved Oxygen Radical Absorbance Capacity (ORAC) Assay using Fluorescein as a New Fluorescent Probe", Brunswick Laboratories, 2001, Wareham, MA 02571, pp. 1-31.
McDaniel, D.H. et al.: "Idebenone: a new antioxidant—Part 1. Relative assessment of oxidative stress protection capacity compared to commonly known antioxidants" Journal of Cosmetic Dermatology, Blackwell Science, Oxford, GB, vol. 4, No. 1, Jan. 1, 2005, pp. 10-17.
David P. T. Steenvoorden et al., "The use of endogenous antioxidants to improve photoprotection", New Trends in Photobiology (Invited review), Journal of Photochemixtry and Photobiology B: Biology 41 (1997), pp. 1-10.
"Skin Diseases Associated with Oxidative Injury"; Oxidative Stress in Dermatology; pp. 323 ff, Marcel Decker Inc., New York, Publisher: Juergen Fuchs, Frankfurt and Lester Packer, Berkeley, California, 1993.
A.R. Young: "Methods Used to Evaluate the Immune Protection Factor of a Sunscreen: Advantages and Disadvantages of Different in Vivo Techniques", St. John's Institute of Dermatology, King's College, London, England, vol. 74, Nov. 2004, pp. 19-23.
J. Wenk et al., "UV-induced Oxidative Stress and Photoaging", Oxidants and Antioxidants in Cutaneous Biology, Curr Probl Dermatol Basel, Karger, 2001, vol. 29, pp. 83-94.
K. Scharffetter-Kochanek et al., "Photoaging of the skin from phenotype to mechanisms", Experimental Gerontology 35 (2000), pp. 307-316.
E. Wieland et al., "Idebenone protects hepatic microsomes against oxygen radical-mediated damage in organ preservation solutions", Transplantation vol. 60, pp. 444-451, Sep. 15, 1995.
Diffey, "Has the Sun Protection Factor had its Day?", British Medical Journal; Jan. 15, 2000, 320, 7228, Research Library, p. 176-177.
Federal Register, 43 (166), p. 38206-38269, Friday, Aug. 25, 1978, Part ll Dept. of Health, Education and WElfare, Food and Drug Admin. "Sunscreen Products for Over-The-Counter Human Drugs, Proposed Safety, Effective and Labeling Conditions".

* cited by examiner

*Primary Examiner* — Michael G Hartley
*Assistant Examiner* — Melissa Perreira
(74) *Attorney, Agent, or Firm* — Leydig, Voit & Mayer, Ltd.

(57) ABSTRACT

A method for characterizing an oxidative stress protective capacity of an antioxidative substance includes assigning a first score indicative of an oxidative stress protective capacity of a first antioxidative substance. The first score is based on the performance of the first antioxidative substance in a first antioxidative efficacy test relative to the performance of a second antioxidative substance in the first antioxidative efficacy test.

10 Claims, 3 Drawing Sheets

METHOD FOR CHARACTERIZING THE OXIDATIVE STRESS PROTECTIVE CAPACITY OF AN ANTIOXIDATIVE SUBSTANCE

The present invention relates in general to oxidative stress in human skin, and in particular to a method for characterizing the oxidative stress protective capacity of an antioxidative substance, such as an antioxidant, or of a topical skin preparation including an antioxidative substance.

BACKGROUND

Human skin is susceptible to oxidative stress due to various causes, such as external environmental stressors including exposure to ultraviolet radiation, air pollution, cigarette smoke, chemicals, cosmetics, drugs, ozone and even oxygen itself, as well as to internal stress due to natural biological processes.

For example, the damaging effect of the ultraviolet (UV) part of solar radiation on the skin is well recognized. UV radiation is known to be the predominant cause of premature aging of the skin. UV radiation may lead to photochemical reactions, wherein then the photochemical reaction products intervene in the skin mechanism. Predominantly such photochemical reaction products are free-radical compounds, for example hydroxy radicals. Also, undefined free-radial photoproducts, which are produced in the skin itself, may trigger uncontrolled side reactions due to their high reactivity. Furthermore, lipid peroxidation products, such as for example hydroperoxides and aldehydes, are produced. Free-radical chain reactions may be triggered, resulting in skin damage.

Moreover, UV radiation is ionizing radiation. Hence, there is the risk that ionic species are produced on UV exposure, which species in turn are able to intervene oxidatively in the biochemical processes.

In additional to externally generated oxidative stress, internally generated oxidative stress may occur as a natural by-product of cellular energy production. Both internal and external oxidative stress leads to inflammatory pathways mediated by the formation of free radicals (molecules with unpaired electrons that are highly reactive) that, left unchecked, can cause severe cellular damage to cell membranes, lipids, proteins and DNA. The superoxide radical, a natural by-product of metabolic energy production, causes serious deleterious effects to living cells if not quenched, neutralized or reduced almost immediately after production. It is known that lipid peroxidation is a major problem in biological systems. Protecting against cell membrane oxidation is of paramount importance in living biological systems since the cell membrane is the cell's first line of defense against oxidation The lifetime summation of damage caused by run-away free radicals is one of the main theories of aging, "the damage accumulation theory of aging". There is therefore a high interest in modern medicine regarding the use of antioxidants, substances that scavenge and eliminate free radicals, to counter the deleterious effects (i.e., aging) of the free radical mediated inflammatory pathways caused by oxidative stress.

Oxidative damage to the skin and its more detailed causes are discussed in J. Fuchs et al., "Skin Diseases Associated with Oxidative Injury" in "Oxidative Stress in Dermatology", 1983, pp. 323 et seq.

Antioxidants are substances, to include free radical absorbers or scavengers, that prevent oxidation processes, including oxidation of a molecule such as a lipid, lipoprotein, protein or DNA, or autooxidation of fats containing unsaturated compounds. Various antioxidants are used in the field of cosmetics and pharmacy. These include, for example tocopherol, kinetin, ubiquinone, ascorbic acid, lipoic acid sesamol, colic acid derivatives, butylhydroxy anisole and butylhydroxy toluene. Antioxidants can thus help protect human cells, such as skin cells, from both externally and internally generated oxidative stress.

Topical application of antioxidants is used to optimize the cutaneous antioxidative capacity and to limit skin damage. In vitro and in vivo studies have demonstrates antioxidative and photoprotective properties of antioxidants. See K. Scharffetter-Kochanek et al., "Photoaging of the skin from phenotype to mechanisms", Exp Gerontol 2000, 35:307-316; and J. Wenk et al., "UV-induced oxidative stress and photoaging", Curr Probl Dermatol 2001, 29:83-94. Accordingly, antioxidants may be incorporated in the cosmetic or dermatological formulations.

U.S. Pat. No. 6,756,045 describes treating skin changes, for example involving oxidative processes, using idebenone.

SUMMARY OF THE INVENTION

Antioxidants have become increasingly popular in anti-aging cosmeceuticals. Consumers may be generally familiar with some or many of the topical antioxidants marketed today, including vitamin C, vitamin E, co-enzyme Q10, and alpha lipoic acid. However, consumers do not understand which antioxidants are the most effective, as little scientific research has been conducted on the wide variety of skincare products that contain these ingredients.

Additionally, consumer products may contain various substances that function to protect the skin from external environmental stressors, including oxygen itself, by blocking a stressor from contacting or penetrating the skin. For example, sun screen preparations may contain substances that help protect the skin by blocking all or some ultraviolet radiation from reaching and/or penetrating the skin. Such environmental stressor blocking agents may therefore have a protective, including preventive, effect against oxidative stress in the skin related to external environmental stressors.

What is needed is a standard way to compare the efficacy of antioxidative substances or antioxidative substance-containing preparations in a way that consumers can understand. Such an antioxidative substances may include an antioxidant, photoprotective, or another substance that has a protective effect against externally generated and/or internally-generated oxidative stress.

The present invention provides a method for characterizing an oxidative stress protective capacity of an antioxidative substance. The method includes assigning a first score indicative of an oxidative stress protective capacity of a first antioxidative substance. The first score is based on a performance of the first antioxidative substance in a first antioxidative efficacy test relative to a performance of a second antioxidative substance in the first antioxidative efficacy test.

The present invention also provides another method for characterizing an oxidative stress protective capacity of an antioxidative substance. The method includes:

assigning a first score indicative of an oxidative stress protective capacity of a first antioxidative substance, the first score being based on a performance of the first antioxidative substance in a first antioxidative efficacy test;

assigning a second score indicative of an oxidative stress protective capacity of the first antioxidative substance, the second score being based on a performance of the first antioxidative substance in a second antioxidative efficacy test; and combining the first and second scores so as to provide a total score characterizing the oxidative stress protective capacity of the first antioxidative substance.

The present invention also provides another method for characterizing an oxidative stress protective capacity of an antioxidative substance. The method includes assigning a first score indicative of an oxidative stress protective capacity of a first antioxidative substance. The first score is based on a performance of the first antioxidative substance in a first antioxidative efficacy test relative to first standard indicative of unprotected human skin.

The present invention also provides a method for informing a purchaser of an antioxidative substance of an oxidative stress protective capacity of the antioxidative substance. The method includes providing a score indicative of an oxidative stress protective capacity of a first antioxidative substance, and making an information including the score available to the purchaser.

Also provided by the present invention is a method for marketing a topical skin preparation. The method includes providing the preparation, the preparation including a first antioxidative substance, and providing information including a score indicative of an oxidative stress protective capacity of the first antioxidative substance.

The method according to the present invention addresses the need for standardized information regarding the topical efficacy of antioxidative substances, including antioxidants and other oxidative stress protective substances, as well as preparations containing them. The present invention provides a standardized comparison of different antioxidative substances regarding their topical oxidative stress protective capacity, i.e., their oxidative stress protective capacity in topical applications. The present invention thus provides a simple way for consumers to recognize the level of oxidative/environmental stress protection to be expected from an antioxidative skincare product, and to compare efficacy of topical antioxidative cosmeceutical products.

DETAILED DESCRIPTION

Figure 1:
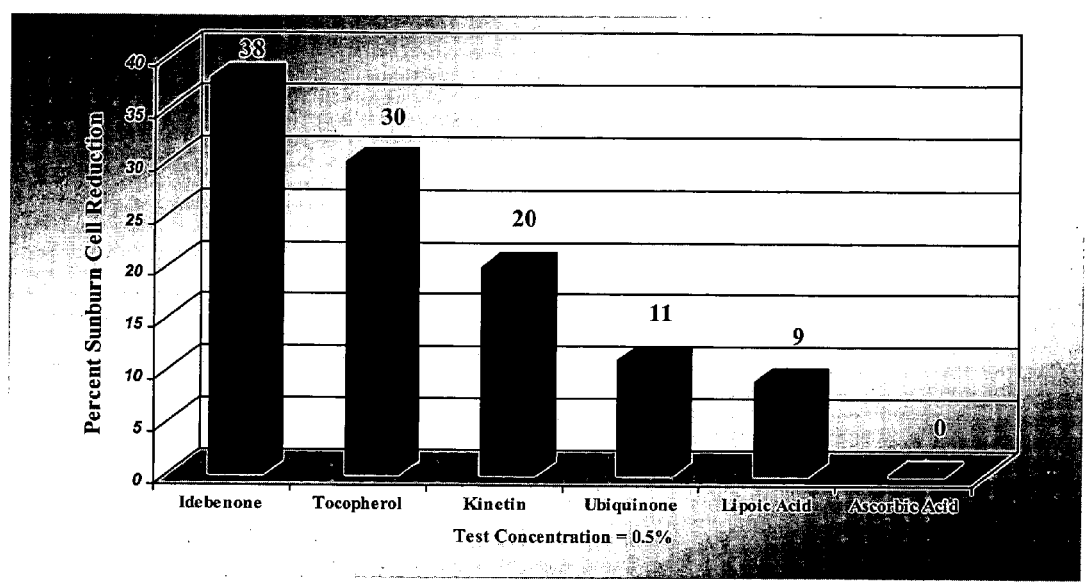
FIG. 1 shows a graph depicting percent reduction in sunburn cell (SBC) formation with application of test substances under ultraviolet B (UVB) irradiation of human skin.

In an embodiment of the present invention six antioxidants were each subjected to five independent antioxidative efficacy tests, or studies. The following antioxidants were tested: idebenone (6-(10-hydroxydecyl)-2,3-dimethoxy-5-methyl-1,4-benzoquinone) dl-alpha tocopherol (vitamin E); kinetin (a plant derivative); ubiquinone (coenzyme Q-10); 1-ascorbic acid (vitamin C) and dl-alpha lipoic acid. The five tests were used to assess the oxidative stress protective capacity of each antioxidant. The results of the five tests for each antioxidant were combined so as to provide a total score indicative of overall performance of each antioxidant.

The tests included one in vivo test (Test 1) and four in vitro tests (Tests 2-5).

Test 1, UVB irradiation of human skin measuring damage by formation of sunburn cells ("sunburn cell assay") tested in vivo the ability of each antioxidant to protect against UV induced oxidative stress. In Test 2, radical scavenging capacity measured by photochemilluminescence ("photochemilluminescence"), the ability of the antioxidant to suppress free radical formation was assessed. Test 3, LDL pro-oxidative systems measuring primary oxidation by-products ("primary oxidative products"), assessed the antioxidant's ability to suppress lipid oxidation. Test 4, microsome pro-oxidative system measuring secondary oxidation by-products ("secondary oxidative products"), assessed the antioxidant's ability to protect against cell membrane oxidation. In in vitro Test 5, UVB irradiation of keratinocytes measuring DNA damage ("UVB irradiated keratinocytes"), the antioxidant's ability to protect against UV induced oxidative stress was assessed.

Each oxidant was scored in each test, the results were then totaled for each antioxidant for each of the tests on an equal weighted basis. The total score of a particular antioxidant is reflective of the overall oxidative stress protective capacity of the antioxidant.

The five tests, which were equally weighted at 20 points each, allowed for the maximum highest possible score of 100 points. Using this scale, the higher score indicates higher oxidative stress protective capacity of the antioxidant. Equal weight was given to an antioxidant's performance in each study because each study tested the antioxidant's ability to protect against a unique different set of oxidative stress parameters. To assign scores, the performance of the antioxidant that demonstrated the greatest benefit for a specific test conducted was used as the standard for that test and received a score of 20 points. The results of the remaining antioxidants in that test were normalized to the standard by assigning each antioxidant a score equal to a percentage of the 20 points based on their performance relative to the standard in that test.

The following provides a brief summary of the protocol for each test conducted:

Test 1: UVB Irradiation of Human Skin Measuring Damage by Formation of Sunburn Cells (SBC)

Exposure to UV radiation can cause damage of epidermal cells, resulting in the formation of sunburn cells. Since sunburn cells can be counted, their formation provides a relatively sensitive and quantitative measure of the extent of UV radiation damage to the epidermis.

Treatment

All applications were made to a 5×10 cm area site over the mid-back region once a day for two weeks. Each putative antioxidant was applied to five (n=5) different healthy adult volunteers between the ages of 18 and 60. All Antioxidants were dissolved in ethanol/water at 0.5% w/w concentrations. Additionally, one test site was left untreated and served as a control. Approximately ten minutes after the last application, test sites were irradiated to 1.5 MED (Minimal Erythema Dose) of UVB light, a shave biopsy taken and prepared histologically, and the number of sun burn cells (SBC) evaluated microscopically per High Power Field.

Light Source

The light source used was a 150 watt xenon arc solar simulator equipped with a UV reflecting dichromic mirror and a 1 mm thick Schott WG-320 (BES Optics Inc., W. Warwick, R.I.) filter to produce simulation of the solar spectrum. A 1 mm thick UG5 filter was added to remove reflected heat and remaining visible radiation.

MED Determination

The MED for each subject was determined by exposing a 1 cm diameter circle to untreated areas to a series of exposures in 25% dose increments from the solar simulator. The MED was defined as the time of exposure required to produce a minimally perceptible erythema 20±4 hours after exposure. Biopsies: Approximately ten minutes after the last topical application of the putative antioxidant, a circular area measuring 1 cm in diameter was exposed to a single dose of 1.5 MED using the solar simulator. Approximately 20 hours later, a shave biopsy (~4×4 mm) was obtained from each irradiated and untreated control sites. Following injections of a local anesthetic (lidocaine). The skin specimens were immediately fixed in 10% buffered formalin.

Histology

The fixed specimens were processed routinely, embedded in paraffin and then sectioned and stained with hematoxylin-eosin. The numbers of sun burn cells (SBC) were determined in at least 12 sections at 50 u intervals. A minimum of 70 high power fields (HPF) was counted from each biopsy and the average number of SBCs per HPF determined. All specimens were counted in a blinded manner.

Figure 3:
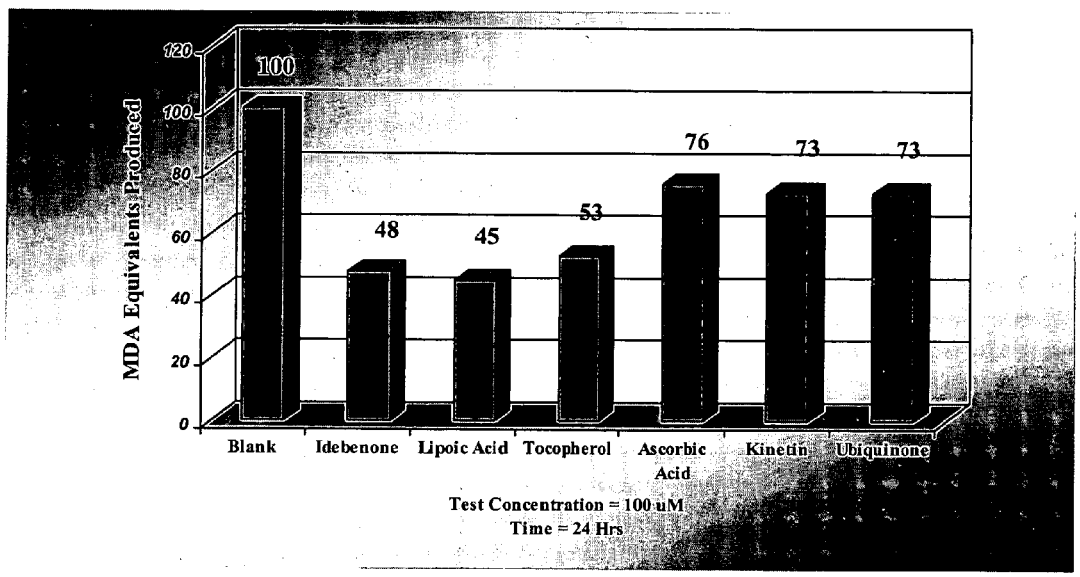
FIG. 3 shows a graph depicting the relative amount of secondary oxidation by-products (MDA equivalents) in the presence of test substances as percentage compared to the BLANK (control, i.e., incubation without addition of antioxidants) in a microsome pro-oxidation system.

FIG. 3 expresses the photoprotective benefits of the antioxidants tested based on the percent change over baseline (delta percent) for the number of SBC per HPF.

Test 2: Radical Scavenging Capacity Measured by Photochemilluminescence

This test assessed the general antioxidative capacity of substances in their ability to scavenge free radicals via the measurement of radicals generated (or lack thereof) through their reaction with luminol and subsequent light emission.

The individual antioxidant capacity of the putative antioxidant substances was estimated by the Photochem® system (Analytik Jena AG, Jena, Germany, and Analytik Jena USA, Inc., Texas). The system combines the generation of radicals through photochemical excitation with highly sensitive luminometric detection via the radical reaction with luminol to produce measurable light emission. Samples are diluted with pre-made buffers (standardized kits) and applied to the device. The relative antioxidative capacity is determined by comparison to a standardized blank (without antioxidants) and a standard provided with the kit. The ACL-kit (Integral Antioxidative Capacity of lipid-soluble substances) and the ACW-kit ((Integral Antioxidative Capacity of water-soluble substances) were used.

Antioxidant concentrations effective to eliminate radical formulation were established for each antioxidant. Table 1 summarizes the results.

TABLE 1

Radical Scavenging Capacity Measured by Photochemilluminescence

| Antioxidant Substance | Effective Concentration (nmol/L) |
|---|---|
| Idebenone | 10 |
| Ascorbic acid | 10 |
| Tocopherol | 10 |
| Ubiquinone | 100 |
| Kinetin | 100 |
| lipoic acid | >1000 (not detectable) |

Test 3: LDL Pro-Oxidative Systems Measuring Primary & By-Products

This test assessed the ability of the antioxidant to protect LDL stressed with Copper Sulfate ($Cu-SO_4$) oxidative system. The $CuSO_4$-LDL system was used to evaluate the protection of lipid bulks over time measuring the primary by-products of lipid peroxidation—the highly reactive and cytotoxic lipid hydroperoxides.

Isolation of LDL

Low Density Lipoproteins (d=1.019-1.063 kg/L) were isolated in clean Beckman one-way Quick-Seal© Tubes (Beckman Coulter Inc., Palo Alto, Calif.) by ultracentrifugation from pooled plasma of healthy donors using an established protocol. After isolation, LDLs were extensively dialyzed against a degassed and nitrogen-saturated Tris-Hydrochloric (HCl) buffer (5 mmol/L, pH7.4) containing 1 mmol/L EDTA. Before oxidation by $CuSO_4$, EDTA was removed from LDL by dialysis against a Tris-HCl buffer (5 mmol/L, pH7.4) without added EDTA.

Incubation LDL with the Pro-Oxidant System Ham'sF-10/$CuSO_4$

LDL oxidation was achieved by incubating (37° C., 95% $O_2$, 5% $CO_2$) 1 g of LDL protein/L with and without the putative antioxidant substances (at equivalent 100 μmol concentrations) in 2 ml of serum-free Ham's F-10 medium (BioSource International, Camarillo, Calif.) in the presence of 20 μmol/L $CuSO_4$ for the times indicated in the figure legends.

Measurement of Lipid Hydroperoxides

Lipid hydroperoxides were determined with the Cayman Lipid Peroxidation (LPO) Assay Kit (Cayman Chemical, Ann Arbor, Mich.) which measures the hydroperoxides directly utilizing the redox reactions with ferrous ions to produce ferric ions which can be detected using thiocyanate ion as the chromogen.

Figure 2:
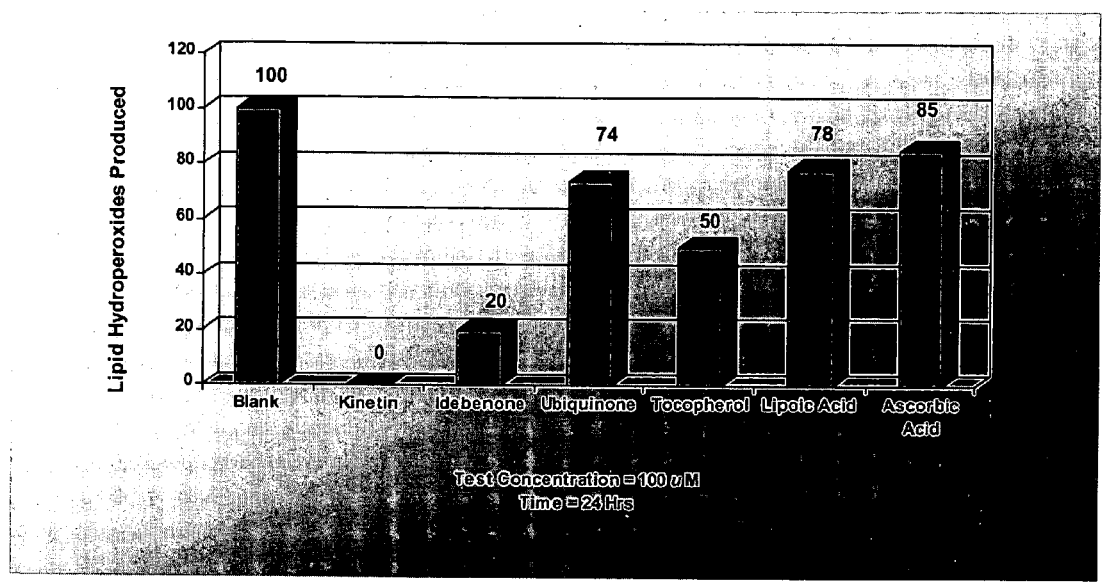
FIG. 2 shows a graph depicting the relative amount of primary oxidation by-products (lipid hydroperoxides) in the presence of test substances as percentage compared to the BLANK (control, i.e., incubation without addition of antioxidants) in a low density lipoprotein (LDL) pro-oxidative system.

FIG. 2 shows the antioxidative effect of the substances as percentage compared to the BLANK control (incubation without addition of antioxidants).

Test 4: Microsome Pro-Oxidative System measuring Secondary Oxidation By-Products In this test, an assessment of antioxidative ability to protect microsomal membrane stressed with NADPH/ADP/$Fe^{3+}$-oxidative system measuring secondary oxidative by-products (Malondialdehyde-MDA equivalents) was performed utilizing the Thiobarbituric Acid Reactive Substances (TBARS) method. See E. Wieland et al., "Idebenone protects hepatic microsomes against oxygen radical-mediated damage in organ preservation solutions", Transplantation, September 1995, 15, 60(5):444-51, the subject matter of which is hereby incorporated by reference herein. Antioxidants protecting bulky lipids, such as low density lipoproteins, are not necessarily good protectors of cell membranes due to their hydrophilic/lipophilic bilayer composition. Therefore the pro-oxidative NADPH/ADP/$Fe^{3+}$-microsome system was used as an in vitro model system more closely resembling natural cellular biological systems. Oxidation of cell membranes leads to serious consequences in altering cell membrane fluidity and cell function.

Preparation of Microsomes

Livers were obtained from male Wistar rats weighing between 250 and 400 g. Tissue was homogenized in 50 mmol/L N-2-Hydroxyethylpiperazine-N-2-Ethanesulfonic Acid (HEPES), 250 mmol/L sucrose buffer, pH 7.4, containing 150 mmol/L Potassium Chloride (KCl) and 500 μmol/L EDTA using a kinematica polytron PT3000 (Brinkmann Instruments, Westbury, N.Y.) homogenizer. Microsomal vesicles were isolated by removal of the nuclear fraction at 8,000×g for 10 min at 4° C. and removal of the mitochondrial fraction at 18,000×g for 10 min at 4° C. using a Beckman L8-55 ultracentrifuge and a 50Ti-13 rotor. The microsomal fraction was sedimented at 105,000×g for 60 min at 4° C. The pellet was washed once in 50 mmol/L HEPES and 150 mmol/L KCl, pH7.4, and collected again at 105,000×g for 30 min. The resulting microsomal pellet was resuspended in HEPES/KCl, pH7.4, by careful sonication in ice and stored in portions (10 mg protein/ml) at −80° C. until use.

Incubation of Microsomes with the Pro-Oxidant System NADPH/ADP/$Fe^{3+}$

The microsomal preparations were incubated in the presence of the pro-oxidant system NADPH/ADP/$Fe^{3+}$, consisting of 0.20 mmol/L NADPH, 50 mmol/L ADP, and 0.25 mmol/L $FeCl_3$ in HEPES/KCl buffer (150 mmol/L KCl, 50 mmol/L HEPES) with and without the putative antioxidant substances. Oxidation of 1-ml aliquots containing 1 mg of protein was started at 37° C. by the addition of NADPH and was stopped with EDTA (10 mmol/L) after the times indicated in the figure legends. Control incubations without the pro-oxidant system were performed at 37° C. in the presence of EDTA. All Antioxidants were dissolved in water or ethanol and added to the incubations at equivalent 100 μmol concentrations.

Measurement of Secondary Oxidation Products, MDA Equivalents or TBARS Method

Microsomal preparations (500 μl) were mixed with 1 ml of thiobarbituric acid (0.67 g/100 ml, 0.05 mol/L Sodium Hydroxide-NaOH). After the addition of trichloroacetic acid (50% w/v), the samples were heated to 90° C. for 30 min. After cooling and extraction of the samples with 1 ml of butanol, the absorbance of the butanol phase was determined spectrophotometrically at 532 nm. For quantification, an external standard curve was prepared using 1,1,3,3-tetraethoxypropane, which yields MDA.

FIG. 3 shows the antioxidative effect of the substances as percentage compared to the BLANK control (incubation without addition of antioxidants).

Test 5: UVB Irradiation of Keratinocytes Measuring DNA Damage

This test assessed DNA damage in cell culture experiments under pro-oxidative conditions (UVB irradiation of human keratinocytes) by measuring the positive cells for anti-thymine dimer antibodies. This experiment is thought to reflect a direct correlation to the in vivo occurring DNA cross linking damage following UVB exposure and the protection of such nuclear damage by antioxidants.

Keratinocyte Collection

Human primary foreskin keratinocytes (second passage) were grown in 6-well plates containing cover slips to 60% confluence in serum free medium (KGM, Clonetics) containing 0.07 mM $CaCl_2$. Six hours before UVB-radiation medium was removed and replaced by fresh growth medium with or without the antioxidative substances. The concentrations of the antioxidants are indicated in the figures.

Ultraviolet Light (UVB) Irradiation of Keratinocytes

Keratinocyte cultures were irradiated with a single dose of 200 mJ/cm2 UVB, using FS-20/T-12 bulbs (emission range: 280-340 nm; 305 nm max.). Immediately prior to irradiation, the medium was replaced with 1 ml sterile PBS (pH 7.4, 37° C.), and after irradiation, PBS was replaced with fresh growth medium. UVB exposure was quantitated using a Goldilux Ultraviolet radiometer. Cells were maintained at 37° C. (5% $CO_2$) for 1 hour until fixation with paraformaldehyde (PFA).

Fixation and Nuclear Thymine Dimer Staining of Keratinocytes

Cells were fixed with 4% PFA in PBS for 30 min at RT, washed with PBS and permeabilized by incubation with EtOH/PBS (90/10; v %/v %) for 30 min at ~10° C. After fixation and permeabilization cells were washed twice with PBS containing 1% of bovine serum albumin (BSA). They were then incubated for 30 min with 10 μg/ml anti-thymine Dimer Ab (clone KTM53; Kamiya) at RT. After the incubation period cells were washed twice with PBS-BSA and incubated for 30 min with 20 μg/ml secondary FITC-conjugated anti-mouse IgG at RT. After the incubation with the secondary antibody, cells were washed twice with PBS-BSA and fixed again with 4% PFA for 15 min at RT. Slides were analyzed by confocal microscopy.

This experiment is thought to reflect the in-vivo occurring DNA damage following UVB exposure and the protection of such nuclear damage by antioxidants. Table 2 shows the results, which may be seen as approximate estimations of the occurrence of nuclear thymine dimer photo products.

TABLE 2

UVB Irradiation of Keratinocytes Measuring DNA Damage

| Antioxidant Substance | Positive cells after UVB radiation* | Inhibition of photoproduct generation (protective effect) |
| --- | --- | --- |
| No-radiation control | 0% | 100% |
| Idebenone | 29% | 45% |
| Ascorbic acid | 34% | 36% |
| Kinetin | 34% | 36% |
| Tocopherol | 35% | 34% |
| Ubiquinone | 51% | 4% |
| lipoic acid | 53% | 0% |
| 200 mJ/$cm^2$ UVB radiation | 53% | 0% |

* = percentage of positive cells (above threshold) in three fields (counted cell number~120–150)

Collation of Test Results

Idebenone produced the greatest benefit in Test 1, the sun burn cell assay, producing a 38% reduction in SBCs. Therefore, idebenone's performance was selected as the standard and assigned 20 points. Tocopherol was second, producing a 31% reduction in SBCs. To determine the relative activity (efficacy) of tocopherol to the standard, idebenone's results, the percentage reduction achieved by tocopherol was divided by the percentage reduction achieved by idebenone: 31/38× 100=82% relative activity. Therefore, tocopherol received 82% of the 20 points or 16 points (rounded to the nearest whole number).

Because the Test 2, photochemilluminescence, results are expressed as the lowest effective concentration and a base 10 serial dilution was used, the scores were assigned as follows: 10 nmol/L=20; 100 nmol/L=15; 1000 nmol/L=10; >1000 nmol/L=5.

A total oxidative stress protective capacity score for each antioxidant was determined by adding the results of the five tests for each antioxidant. Each of the five tests was assigned equal weight. That is, each antioxidant could receive a maximum of 20 points in each test so that each test contributed equally to the total score for each antioxidant. The total scores, and thus, relative oxidative stress protective capacity of the respective antioxidants tested are summarized in Table 3.

TABLE 3

Global Relative Antioxidant Activity: Total Oxidative Stress Protective capacity Scores

| Test | Idebenone | Tocopherol | Kinetin | Ubiquinone | Ascorbic acid | Lipoic acid |
|---|---|---|---|---|---|---|
| Sun Burn Cell Assay | 20 | 16 | 11 | 6 | 0 | 5 |
| Photochemilluminescence | 20 | 20 | 10 | 15 | 20 | 5 |
| Primary Oxidative Products | 16 | 10 | 20 | 5 | 3 | 4 |
| Secondary Oxidative Products | 19 | 17 | 10 | 12 | 12 | 20 |
| UVB Irradiated Keratinocytes | 20 | 17 | 17 | 17 | 17 | 7 |
| Total Points (Total Score) | 95 | 80 | 68 | 55 | 52 | 41 |

In embodiments of the present invention, different numbers and types of antioxidative efficacy tests may be performed in arriving at total scores for antioxidant substances tested. An antioxidative efficacy test may be any test that directly or indirectly provides information regarding the oxidative stress protective capacity of an antioxidative substance tested. The oxidative stress protective capacity of an antioxidative substance may in some cases be function, for example, of its ability to prevent an environmental stressor from reaching and/or penetrating the skin. In other cases, the oxidative stress protective capacity of an antioxidative substance may, for example, be a function of its ability to prevent or reduce an oxidation process in the skin.

Other antioxidants than the antioxidants tested in the embodiment described in detail above may be tested. In particular, antioxidants that are suitable or conventional for cosmetic and/or dermatological applications may be tested. Such anti-oxidants include, for example, one or more of the following: antioxidant enzymes (for example superoxide dismutase, catalase, glutathione peroxidase, glutathione S-transferase, glutathione reductase), antioxidant botanical extracts (for example green tea, white tea, black tea, licorice, grape, bilberry), plant growth factors (for example N-furfuryladenine), amino acids (for example glycine, histidine, tyrosine, tryptophan) and their derivatives, imidazoles (for example urocanic acid) and their derivatives, peptides, such as D,L-carnosine, D-carnosine, L-camosine and their derivatives (for example anserine), carotinoids, carotenes (for example alpha-carotene, beta-carotene, lycopene) and their derivatives, chlorogenic acid and its derivatives, lipoic acid and its derivatives (for example dihydrolipoic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, gamma-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) and sulphoximine compounds (for example buthionine sulphoximines, homocysteine sulphoximine, buthionine sulphones, pentathionine sulphoximine, hexathionine sulphoximine, heptathionine sulphoximine) in very low, acceptable doses (for example pmole to μmoles/kg), also (metal) chelating agents (for example alpha-hydroxy fatty acids, palmitic acid, phytic acid, lactoferrin), alpha-hydroxy acids (for example citric acid, lactic acid, malic acid, mandelic acid, gluconolactone, lactobionic Acid), humic acid, colic acid, colic extracts, bilirubin, biliverdin, EDTA, EGTA and their derivatives, unsaturated fatty acids and their derivatives (for example gamma-linolenic acid, linolic acid, oleic acid), folic acid and their derivatives, ubiquinone and ubiquinol and their derivatives, vitamin C and derivatives (for example ascorbyl palmitate, Mg-ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (for example ZnO, $ZnSO_4$), selenium and its derivatives (for example selenium methionine), stilbenes and their derivatives (for example stilbene oxide, trans-stilbene oxide) and suitable derivatives (salts, esters, ethers, sugars, nucleotides, nucleosides, peptides and lipids) of these said active ingredients.

In the embodiment of the present invention described in detail above, the performance of an antioxidant with the best result relative to the results of the other antioxidants in a given antioxidative efficacy test served as the standard for that test. For example, idebenone produced the greatest percent reduction in sun burn cells (SBCs) in the sunburn cell assay (Test 1) and its performance was selected as the standard, receiving 20 points. Kinetin performed better than the other antioxidants in the primary oxidative products test (Test 3), so Kinetin's performance was selected as the standard, receiving 20 points in that test. In other embodiments of the present invention, the performance of the same antioxidative substance, such as idebenone, irrespective of whether or not its performance is the best, may be selected as the standard in every test performed. One or more tests may be performed.

In embodiments of the present invention, the performance of a single antioxidative substance subjected to one or more tests relative to a standard, or to a respective standard for each test, may be used to assign a score indicative of the oxidative stress protective capacity of the antioxidative substance. The scores from the tests may be summed to give a total score. According to the present invention, results or scores may be combined in any of a variety of ways to give a total score characterizing an antioxidative substance is within the scope of the present invention.

In an embodiment of the present invention, a score indicative of the oxidative stress protective capacity of the antioxidative substance may be assigned based on the performance of the antioxidative substance in an antioxidative efficacy test relative to a standard indicative of unprotected human skin. The result of the antioxidative efficacy test performed on a control may serve as a standard indicative of unprotected human skin. For example, the number of sunburn cells (SBCs) produced under UV radiation exposure of untreated skin in the sunburn cell assay (Test 1) may be used as the control. Other standards, whether or not indicative of unprotected human skin, are possible. For example, a standardized blank in the Photochem® system may serve as the standard for the photochemilluminescence test (Test 2). Any of a variety of controls or standards in any of a variety of antioxidative efficacy tests may be used according to the present invention.

A variety of scoring and weighting methods may be employed in other embodiments of the present invention. For example, alphabetical, alpha-numeric or other symbological or graphical indicators, such as pie chart, bar graphs, or numbers of stars, numbers of "smiley faces", etc., could be used as scores. The weighting of the test results could be adjusted, for example, for optimal clinical correlation based on the specific tests or experiments performed.

In the embodiment of the present invention described in detail above, individual test scores and a total score was assigned to each antioxidant. In other embodiments of the present invention, the oxidative stress protective capacity of an antioxidative substance-containing topical preparation as a whole may be characterized by performing one or more antioxidative efficacy tests on the entire preparation, rather than on an individual antioxidative substance. Thus according to the present invention an overall score can be assigned to a topical skin preparation, indicative of the antioxidative capacity of the preparation as a whole. Such overall scores assigned to topical skin preparations enable an easy, effective way for consumers to compare the oxidative stress protective capacity of the preparations.

In addition to one or more antioxidative substances, topical skin preparations, such as cosmetic and dermatological preparations, may contain additional components. For example, topical skin preparations may contain cosmetic auxiliaries, as are used conventionally in such preparations, such as preservatives, bactericides, perfumes, substances for preventing foaming, dyestuffs, pigments which have a coloring effect, thickening agents, surfactant substances, emulsifiers, softening, moisturizing and/or moisture-retaining substances, fats, oils, waxes or other conventional constituents of a cosmetic or dermatological formulation, such as alcohols, polyols, polymers, foam stabilizers, electrolytes, organic solvents or silicone derivatives. Topical skin preparations may also contain UV filter substances such as, for example, the following: avenobenzene, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, and zinc oxide. Moreover, topical skin preparations may contain various active ingredients, such as alpha hydroxy acids (AHA), including glycolic acid, lactic acid, malic acid, tartaric acid, citric acid, and the like; beta hydroxy acids (BHA), including salicylic acid and the like; and retinoids, including retinol, retinal, retinyl palmitate, retinoic acid, tazarotene-acetylenic retinoids, and other ester derivatives of Vitamin A and the like. Irrespective of the presence of any such additional components, the present invention enables an overall score to be assigned to the topical skin preparation, indicative of the oxidative stress protective capacity of the preparation as a whole.

While the invention has been described in connection with individual embodiments, it is not intended to limit the scope of the invention to the particular form set forth, but, on the contrary, it is intended to cover such alternatives, modifications and equivalents as may be included within the spirit and scope of the invention as defined by the appended claims.

What is claimed is:

1. A method for characterizing an oxidative stress protective capacity, relative to human skin, of a first antioxidative substance, the method comprising:
   providing a first result based on a performance of the first antioxidative substance in a first antioxidative efficacy test, the first antioxidative efficacy test measuring a first parameter associated with oxidative stress;
   assigning, based on the first result, a first score indicative of an oxidative stress protective capacity, relative to human skin, of the first antioxidative substance;
   providing a second result based on a performance of the first antioxidative substance in a second antioxidative efficacy test, the second antioxidative efficacy test measuring a second parameter associated with oxidative stress;
   assigning, based on the second result, a second score indicative of the oxidative stress protective capacity, relative to human skin, of the first antioxidative substance; and
   combining the first and second scores so as to provide a total score characterizing the oxidative stress protective capacity, relative to human skin, of the first antioxidative substance.

2. The method as recited in claim 1 wherein the first antioxidative substance is at least one of an antioxidant and an environmental stressor blocking agent.

3. The method as recited in claim 1 wherein the first score is based on the performance of the first antioxidative substance in the first antioxidative efficacy test relative to a standard.

4. The method as recited in claim 3 wherein the standard is based on a result of the first antioxidative efficacy test performed on a control.

5. The method as recited in claim 3 wherein the standard is indicative of unprotected human skin.

6. The method as recited in claim 1 wherein the first score is at least one of a numerical, an alphabetical, an alpha-numerical and a symbological score.

7. The method as recited in claim 1 wherein the first antioxidative substance is a topical skin preparation.

8. The method as recited in claim 7 wherein the topical skin preparation includes at least one of an antioxidant and an environmental stressor blocking agent.

9. The method as recited in claim 1 wherein the first and second antioxidant efficacy tests are in-vivo or in-vitro tests.

10. The method as recited in claim 1 wherein the first and second antioxidant efficacy tests include a chemical, physical or instrumental test.

* * * * *